(12) United States Patent
Senga et al.

(10) Patent No.: US 7,691,371 B2
(45) Date of Patent: Apr. 6, 2010

(54) PREPARATION COMPRISING BATROXOBIN FOR INHIBITING LOCAL INVASION OF MALIGNANT TUMORS

(75) Inventors: Hirobumi Senga, Tokyo (JP); Yongling Wan, Beijing (CN); Lishui Chang, Beijing (CN)

(73) Assignee: Tobishi Pharmaceutical Co., Ltd., Tokyo (JP)

( * ) Notice: Subject to any disclaimer, the term of this patent is extended or adjusted under 35 U.S.C. 154(b) by 148 days.

(21) Appl. No.: 11/638,069

(22) Filed: Dec. 13, 2006

(65) Prior Publication Data

US 2007/0104706 A1 May 10, 2007

Related U.S. Application Data

(63) Continuation of application No. PCT/JP2005/012142, filed on Jun. 24, 2005.

(30) Foreign Application Priority Data

Jun. 24, 2004 (JP) ............................. 2004-213636

(51) Int. Cl.
*A61K 38/48* (2006.01)
*C12N 9/48* (2006.01)
(52) U.S. Cl. .................................. 424/94.64; 435/212
(58) Field of Classification Search .............. 424/94.64; 435/212
See application file for complete search history.

(56) References Cited

U.S. PATENT DOCUMENTS

| 4,137,127 A | 1/1979 | Stocker |
| 5,595,974 A | 1/1997 | Tomaru |

FOREIGN PATENT DOCUMENTS

| CN | 1090028 C | 9/2002 |

OTHER PUBLICATIONS

Russian Official Action—2007102570/15(002759).
Korean Office Action—10-2007-7001620.
J. Cancer Res Clin Oncol. 1990;116(2):168-72.
Lysine as a Natural Enzyme Block; p. 38-47.
Journal of the Japanese Society of Pediatric Surgeons (Nippon Shoni Geka Gakkai Zasshi) vol. 36, No. 3, May 2000.
Inhibition effect of snake venom (Batroxobin) on lung metastasis (Hebidoku (Batroxobin) no Hai Ten'l Yokusei Koka) J Cancer and Chemotherapy, 14(3):PART I 732-734; 1987.

The encapsulation of tumours (L.C Barr) (Clin Expl Metastasis 7(3):277-282, 1989).
Morphological evidence for an invasion-independent metastasis pathway exists in multiple human cancers. (Sugino T. et al.) (BMC Medicine, 2(9):1-8, 2004).
Non-invasive thymoma with widespread blood-borne metastasis. (Yoshida A et al.) (Virchows Arch Pathol Anat 390:121-126, 1981).
A case of encapsulated noninvasive thymoma (stage I) with myasthenia gravis showing metastasis after a 2-year dormancy. (Masunaga A et al.) (Surgery Today, Jpn J Surg, 25:369-372, 1995).
Effects of synthetic urokinase inhibitors on local invasion and metastasis in a murine mammary tumor model. (Alonson DF, et al.) (Breast Cancer Res Treat 40:209-223, 1996).
Influence of polyamines on in vitro and in vivo features of aggressive and metastatic behavior by human breast cancer cells. (Manni A, et al.) (Clinical & Experimental Metastasis 19:95-105, 2002).
Fibrinogen assembly, secretion, and deposition into extracellular matrix by MCF-7 human breast carcinoma cells. (Rybarczyk BJ, et al.) (Cancer Research 60:2033-2039, 2000).
Tumors and fibrinogen. The role of fibrinogen as an extracellular matrix protein. (Simpson-Haidaris P.J., et al. (Ann N Y Acad Sci 936:406-425, 2001).
Fibrinogen is an important determinant of the metastatic potential of circulating tumor cells. (Palumbo J.S. et al.) (Blood 96(10):3302-3309, 2000).
Effect of defibrination with batroxobin on growth and metastasis of JW sarcoma in mice. (Chmielewska J., et al.) (Europe J. Cancer 16:919-923, 1980).
Comparsion of the actions of thombin and the thrombin-like venom enzymes ancrod and batroxobin. (Aronson D.L.) (Thrombos. Haemostas. (Stuttg.), 36: 9-13, 1976).
The mechanism of action of a coagulant fraction of Malayan Pot Viper Venom, Arvin, and of reptilase. (Kwaan H.C., et al.)(Thromb Diarh Haemorrh 45 Suppl:63-68, 1971).
Molecular cloning and sequence analysis of cDNA for batroxobin, a thrombin-like snake venom enzyme. (Itoh N., et al.) (J. Biol Chem 262(7):3132-3135, 1987).
Toxicological studies on Batroxobin (Defibrase), a new Defibrinogenic acute toxicity in mice, rats, rabbits and dogs. (Ozaki M., Hiyama T., Kunikane K., Sato S., Tsushima K., and Mori N.) (Pharmacometrics (Oyoyakuri) 25:339-346, 1983).

(Continued)

*Primary Examiner*—Tekchand Saidha
(74) *Attorney, Agent, or Firm*—Husch Blackwell Sanders LLP Welsh & Katz

(57) ABSTRACT

A preparation for inhibiting local invasion of malignant tumors is provided which comprises batroxobin and therefore can inhibit local invasion of malignant tumors. A preparation for encapsulating malignant tumor tissues is also provided which comprises batroxobin and therefore can cause or promote formation of capsule-like tissue around malignant tumor tissues.

10 Claims, 4 Drawing Sheets

OTHER PUBLICATIONS

Mayumi Iwakawa et al., "Datsu Fibrinogen-yaku Batroxobin no Shuyo Ten'i Yokusei Koka to Yuchaku Yokusei Koka," Nippon Shoni Geka Gakkai Zasshi, 2000, vol. 36, No. 3, p. 662.

Masataka Oshiro, "Shuyo no Zoshoku, Ten'i ni Oyobosu Defibrase no Eikyo," Nippon Ketsueki Gakkai Zasshi, 1981, vol. 44, No. 3, pp. 739 to 743.

Masahiko Shibuya et al., "Batroxobin ni yoru Defibrinogenation no Ten'i Yokusei Koka to NK Kassei," Japanese Journal of Cancer and Chemotherapy, 1987, vol. 14, No. 7, pp. 2286 to 2292.

Masahiko Shibuya et al., "Hebidoku (Batroxobin) no Hai Ten'i Yokusei Koka," Japanese Journal of Cancer and Chemotherapy, 1987, vol. 14, No. 3, pp. 732 to 734.

Chmielewska, J. et al., "Effect of defribination with batroxobin on growth and metastasis of sarcoma in mice," European Journal of Cancer, 1980, vol. 16, No. 7, pp. 919 to 923.

Correa, Jr. M.C. et al., "Inhibition of melanoma cells tumorigenicity by the snake venom toxin jararhagin," Toxicon, 2002, vol. 40, No. 6, pp. 739 to 748.

Supplementary European Search Report for related patent application No. EP 05 75 5657.

Lars Ivarsson, Pulmonary Metastasis Formation after Intravenous Tumour Cell Injection in Definrinogenated Rats, Zeitschrift Fur Krebsforschung Und Klinische Onkologie, Springer, Berlin, DE vol. 85, No. 1, 1976.

Shibuya et al., "Antimetastatic Effect of Defibrinogenation with batroxobin depends on the natural killer activity of host in mice" Journal of Cancer Research and Clinical Oncology, 116:168-172 (1990).

Ivarsson, "Pulmonary metastasis formation after trauma" Acta Chirurgica Scandinavica. Supplementum, Almquist and Wiksell Periodical Co., Stockholm, SE vol. 452 Jan. 1, 1976.

Shibuya et al., "Batroxobin ni yoru Defibrinogenation no Ten'l Yokuseo Koka to NK Kassei" Gan to Kagaku Ryoho—Japanese Journal of Cancer and Chemotherapy, Gan to Kagaku Ryoho, Tokyo, JP, vol. 14, No. 7, (1987).

Kawachi., "B15-F10 Melanoma Saibo no hai Ten'l ni Oyobosu batroxobin no Yokusei Koka to NK Saibo no Kan'yo/The Inhibitory Effect of Batroxobinagainst the lung metestasis of the B16-F10 Melanoma cells implanted in the mice in relation to the activity if the NK cell" Nippon IKA daigaku Zasshi—Journal of Nippon Medical School, Tokyo, JP vol. 55, No. 2 (1988).

Donati et al., "Growth and metastasis of the Lewis lung carcinoma in mice defibrinated with batroxobin" European Journal of Cancer vol. 14, pp. 343-347 (1965).

Chmielewska et al., "Effect of defibrination with batroxobin on growth and metastasis of JW sarcoma in mice" European Journal of Cancer vol. 16 Jan. 1, 1980.

PREPARATION COMPRISING BATROXOBIN FOR INHIBITING LOCAL INVASION OF MALIGNANT TUMORS

TECHNICAL FIELD

The present invention relates to a preparation comprising batroxobin for inhibiting local invasion of malignant tumors and for encapsulating malignant tumor tissues.

BACKGROUND ART

In the treatment of malignant tumors, the success rate for removing of primary cancers has risen steadily due to advances in surgery, radiation and chemotherapy. However, even in the early stages of a tumor, malignant tumor cells often scatter and invade locally into adjacent tissues and organs. In this case, even if the primary focus of malignant tumor is removed surgically, recurrence is possible due to residual invading malignant tumor cells; ultimately resulting in death in many cases. In particular, if malignant tumor cells have invaded into a vital organ, they cannot be removed along with normal tissues. So the recurrence rate and death rate are high in these cases. When a malignant tumor occurs in a vital organ, large amounts of tissue including normal tissues are removed in an effort to avoid local invasion, and the function of the vital organ may be lost. Moreover, in the case of malignant tumors with a high degree of malignancy such as melanoma, lung cancer, liver cancer and pancreatic cancer, early diagnosis is difficult. By the time the tumor is diagnosed, the local invasion of malignant tumor has become widespread, making unacceptable for surgical treatment in many cases.

Radiation usually does not demonstrate positive results for treating the local invasion of these malignant tumors. Moreover, the chemotherapy drugs currently in clinical use, such as adriamycin, which act by directly attacking malignant tumor cells, also attack normal cells, and have strong side-effects; a problem for clinical use. Consequently, new preparations for inhibiting local invasion of malignant tumors are expected.

It is generally believed that local invasion is related as follows to the stages of malignant tumors.

(1) In the early stage of malignant tumors, malignant tumor cells proliferate by cell division, resulting in the tumor tissue's growth. This is known as "dysplasia". In histopathological terms, the proliferating malignant tumor cells are localized at this stage, and can be clearly distinguished from the surrounding normal tissues. In most cases, capsule-like tissue forms around the malignant tumor tissues.

Capsule-like tissue is connective tissue formed as a result of the interaction between malignant tumor tissues and normal tissues, separating the malignant tumor tissues from the normal tissues. So it appears that the malignant tumor tissues are surrounded by a capsule. A malignant tumor enveloped by capsule-like tissue is extremely easy to remove by surgery, and the malignant tumor cells are not scattered during the surgery, there is very little risk of the malignant tumor recurring after surgery.

(2) However, as the malignant tumor progresses, the capsule-like tissue is lost, and there is local invasion from the malignant tumor tissues to adjacent surrounding normal tissues and organs, resulting in wider diffusion of the malignant tumor. At this stage, surgical treatment becomes difficult.

Considering the aforementioned relationship between local invasion and the stages of malignant tumors, it has been suggested that malignant tumor therapies that acted by promoting the formation of capsule-like tissue, might be clinically useful. However, no studies of capsule-like tissue formation around malignant tumors have been done focusing solely on local invasion of malignant tumors, and no drugs have been developed that promote such formation (see, for example, Clin. Expl. Metastasis 7:277-282, 1989). This is because in the technical field, local invasion of malignant tumors is generally considered to be a part of malignant tumor metastatic process, and it is believed that drugs that inhibit metastasis should also be able to inhibit local invasion.

Recently, however, pathway of metastasis which does not involve a local invasion process has been discovered in many malignant tumors (see, for example, BMC Medicine, 2(9):1-8, 2004). For example, there have been clinical reports of malignant tumors that metastasize without local invasion (see, for example, Virchows Arch. Pathol. Anat. 390:121-126, 1981 and Surgery Today 25:369-372, 1995). Moreover, drugs that have been reported to be effective in inhibiting local invasion of malignant tumors but are ineffective against metastasis and, in fact, promote metastasis (see, for example, Breast Cancer Res. Treat. 40:209-223, 1996). Conversely, there have been reports of in vivo experiments with drugs that inhibit malignant tumor metastasis but do not inhibit local invasion (see, for example, Clinical & Experimental Metastasis, 19:95-105, 2002). These reports suggest a phenomenon in which local invasion of malignant tumors is not a part of the metastatic process, but instead, that local invasion and metastasis occur as different processes.

From another perspective, much basic and clinical researches have pointed to a close relationship between malignant tumors and the coagulation and fibrinolytic system. For example, microcirculation disorders caused by increased plasma fibrinogen concentration, increased blood viscosity, abnormal blood rheology and other abnormalities of the coagulation and fibrinolytic system, are known to occur in malignant tumor patients. It has also been reported that increased plasma fibrinogen concentration or secretion of fibrinogen by the malignant tumor cells themselves leads to the deposition of fibrinogen or fibrin in the extracellular matrix of the malignant tumor tissue, and that this then acts as part of the extracellular matrix to promote proliferation, invasion and metastasis of the malignant tumor cells (see, for example, Cancer Research 60:2033-2039, 2000; Ann NY Acad. Sci. 936:406-425, 2001 and Blood 96:3302-3309, 2000).

Focusing on this relationship between malignant tumors and the coagulation and fibrinolytic system, it has been reported that batroxobin, a thrombin-like serine protease from *Bothrops atrox moojeni* venom, inhibits proliferation and metastasis of malignant tumors in the same way as Ancrod, another thrombin-like serine protease (see, for example, Eur. J. Cancer 16:919-923, 1980). However, while this report uses tumor weight as an indicator of the inhibitive effect on malignant tumor proliferation, and the number of metastatic foci in organs as an indicator of malignant tumor metastasis, it does not evaluate the local invasion of malignant tumors.

Also in connection with the relationship between malignant tumors and the coagulation and fibrinolytic system, it has been reported that in an experimental model using fibrinogen-deficient mice, malignant tumor metastasis is dependent on fibrinogen and fibrin, but malignant tumor proliferation and local invasion are not dependent on fibrinogen (see, for example, Blood 96:3302-3309, 2000). However, the relationship between batroxobin and local invasion of malignant tumors has not been reported.

DISCLOSURE OF THE INVENTION

It is therefore the object of the present invention to provide a new drug capable for inhibiting local invasion of malignant tumors, as well as a new drug capable for causing capsule-like tissue formation or for promoting capsule-like tissue formation around malignant tumor tissues.

To resolve these issues, the inventors in this case discovered as a result of exhaustive research into local invasion of malignant tumors in vivo that batroxobin inhibits local invasion of malignant tumors, and causes or promotes the formation of capsule-like tissue around malignant tumor tissues. The present invention is made based on these findings.

That is, the present invention relates to:

(1) a preparation comprising batroxobin for inhibiting local invasion of malignant tumors, and (2) a preparation comprising batroxobin for encapsulating malignant tumor tissues.

BEST MODE FOR CARRYING OUT THE INVENTION

Figure 1:
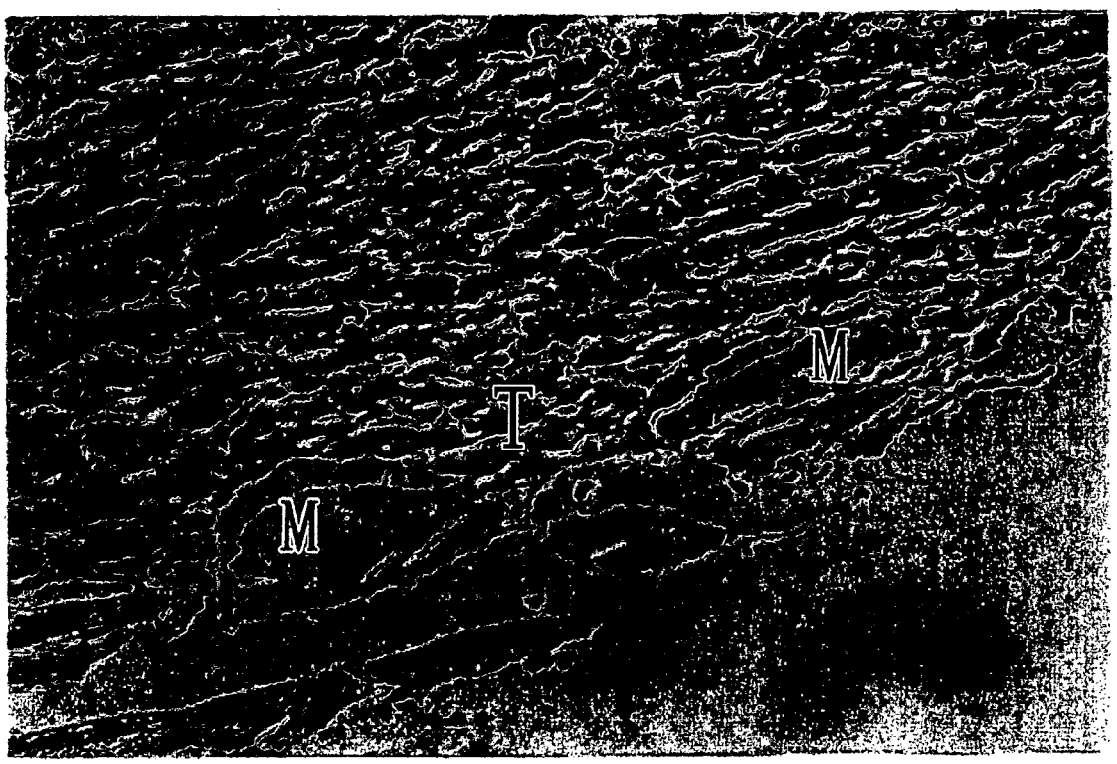
FIG. 1 is a microscopic photo of solid cancer tissues of a B16-BL6 melanoma tumor-bearing mouse in control group.

The present invention is explained in detail below.

In the present invention, the preparation for inhibiting local invasion of malignant tumors and for encapsulating malignant tumor tissues comprises batroxobin as an active component.

Batroxobin is a thrombin-like serine protease derived from venom of *Bothrops atrox moojeni*. Batroxobin releases only fibrinopeptide A from fibrinogen, producing Des A fibrin (also called fibrin I) (see, for example, Thromb. Haemost. 36:9-13, 1976 and Thromb. Diath. Haemorrh. 45 Suppl: 63-68, 1971). Moreover, the primary structure of batroxobin has already been determined (see, for example, J. Biol. Chem. 262(7):3132-3135, 1987).

As with thrombin, batroxobin is a thrombin-like serine protease. However, it differs from thrombin in that while batroxobin releases only fibrinopeptide A from fibrinogen to produce Des A fibrin, thrombin releases fibrinopeptide A and fibrinopeptide B from fibrinogen to produce fibrin. Another difference is that batroxobin does not act on blood coagulation factors other than fibrinogen, while thrombin acts on other blood coagulation factors.

Batroxobin used in the present invention may be naturally occurring preparations or may be products of genetic recombination.

Batroxobin itself is a known substance that can be prepared in accordance with the methods described in Publication of examined Japanese Patent Application No. S57-10718 (Japanese Patent No. 1118129). Alternatively, it can be easily obtained on the market (from Tobishi Pharmaceutical Co., Ltd., Tokyo, Japan and its subsidiary, Beijing Tobishi Pharmaceutical Co., Ltd., Beijing, China).

The targets of the present invention are malignant tumors. Depending on the tissue's original occurrence, malignant tumors can be broadly classified into epithelial malignant tumors and non-epithelial malignant tumors. Non-epithelial malignant tumors can be further classified into malignant tumors derived from mesenchymal tissue, malignant tumors derived from neural tissue and malignant tumors of undifferentiated cells. Specific examples of the each kind of malignant tumors are given below.

Epithelial Malignant Tumors

Adenocarcinomas (carcinomas derived from glandular epithelium, which occur throughout the body including the stomach, intestines, pancreas, trachea, lungs, mammary glands, ovaries, corpus uteri, prostate glands and the like, are supposed to constitute 70 to 80% of human cancers), squamous cell carcinomas (cancers derived from the stratified squamous epithelium and occurring in epithelial tissue of the epidermis, lips, tongue, throat, esophagus, anus, vulva, uterine cervix and the like, and pulmonary squamous epithelial cancers classified as non-small cell lung cancer), basal cell carcinomas (derived from basal cells of the skin and adnexa), transitional cell carcinomas (derived from transitional epithelium, such as bladder cancer), liver cell carcinomas (derived from hepatocytes), renal cell carcinomas (derived from renal epithelium), cholangiocarcinomas (derived from the bile duct) and choriocarcinomas (derived from the placental epithelium)

Non-epithelial Malignant Tumors

Malignant Tumors Derived from Mesenchymal Tissue

Fibrosarcomas (derived from connective tissue and fibrous tissue), liposarcomas (derived from connective tissue and fatty tissue), chondrosarcomas (derived from connective tissue and cartilaginous tissue), osteosarcomas (derived from connective tissue and bone tissue), angiosarcomas (derived from blood vessels), lymphangiosarcomas (derived from lymphoducts), myelogenic leukemia (derived from hemopoietic cells), monocytic leukemia (derived from hemopoietic cells), malignant lymphoma (derived from lymphoid tissue), lymphocytic leukemia (derived from lymphoid tissue), plasmacytoma (multiple myeloma, derived from lymphoid tissue), Hodgkin's cell (derived from lymphoid tissue), leiomyosarcoma (derived from smooth muscle), rhabdomyosarcoma (derived from striated muscle)

Malignant Tumors Derived from Neural Tissue

Neuroblastoma (derived from neuroblasts), medulloblastoma (derived from medulloblasts), malignant astrocytoma (derived from astrocytes), retinoblastoma (derived from retinoblasts), glioblastoma (derived from glioblasts), malignant neurilenoma (derived from Schwann cells), melanoma (derived from neuroectoderm)

Malignant Tumors Derived from Undifferentiated Cells

Malignant teratoma (derived from totipotent cells), nephroblastoma (derived from nephroblasts), hepatoblastoma (derived from hepatoblasts), mixed tumors (derived from various types of cells).

Of these malignant tumors mentioned above, the preparation for inhibiting local invasion of malignant tumors and for encapsulating malignant tumor tissues of the present invention is highly effective against epithelial malignant tumors, and against non-epithelial malignant tumors derived from neural tissue, particularly melanoma and lung cancer.

Local invasion of malignant tumors is defined as invasion that tumor cells break through the capsule to invade into the surrounding fatty tissues and other connective tissues, and it is distinguished from broad invasion (in which the cells invade other organs continuously from the primary tumor).

Encapsulating malignant tumor tissues means that capsule-like tissue is formed around the malignant tumor tissues. Capsule-like tissue is connective tissue formed by interaction between malignant tumor tissues and normal tissues, which cordons off the malignant tumor tissues from the normal tissues so that the malignant tumor tissues appear to be surrounded by a capsule.

Formation of capsule-like tissue around malignant tumor tissues reduces the extirpation extent of tissues during surgical treatment of the malignant tumor, making surgery easier. Since encapsulation facilitates complete extirpation of malignant tumor tissues, tumor recurrence, due to remaining invading tumor cells, can also be prevented. Even when a malignant tumor occurs in a vital organ, loss of the function of the vital organ can be prevented with the present invention, because capsule-like tissue that forms around the malignant tumor tissues, allows the extirpation of malignant tumor tissues in only a minimum area of the organ.

Regarding the causal relationship between batroxobin, an active component of the present invention and the effects of inhibiting local invasion of malignant tumors and encapsulating malignant tumor tissues, there are cases in which local invasion is inhibited without any encapsulation of the malignant tumor tissues (see Examples below). So, encapsulating malignant tumor tissues does not appear to be a necessary condition for inhibiting local invasion of malignant tumors. However, encapsulating malignant tumor tissues seems at least to promote inhibition of local invasion of malignant tumors.

The preparation for inhibiting local invasion of malignant tumors and for encapsulating malignant tumor tissues of the present invention may comprise batroxobin either by itself or combination with other active substances.

Examples of other active substances include antimetabolites such as fluorouracil, antitumor antibiotics such as adriamycin, alkylating agents such as dacarbazine, plant-derived anticancer drugs such as paclitaxel and the like.

Any formulation in the Japanese Pharmacopoeia General Rules for Preparations can be applied to the formulation of the preparation for inhibiting local invasion of malignant tumors and for encapsulating malignant tumor tissues of the present invention. Examples of the formulation of the preparation for inhibiting local invasion of malignant tumors and for encapsulating malignant tumor tissues of the present invention include injections for direct application inside the body (including suspensions and emulsions); ointments (including fatty ointments, emulsion ointments (creams), water-soluble ointments and the like), inhalants, liquids (including ophthalmic solutions, collunarium and the like), suppositories, patches, poultices, lotions and other external formulations; and internal formulations including tablets (including sugar-, film- and gelatin-coated), liquids, capsules, granules, powders (including grains), pills, syrups, troches and the like. These formulations can be prepared by the methods described in the Japanese Pharmacopoeia General Rules for Preparations.

The preparation for inhibiting local invasion of malignant tumors and for encapsulating malignant tumor tissues of the present invention may also include pharmacologically acceptable solid or liquid carriers or interventional therapy bases, depending on its formulation. Examples of pharmacologically acceptable solid or liquid carriers include solvents, stabilizers, preservatives, solubilizing agents, emulsifiers, suspending agents, buffering agents, isotonizing agents, coloring agents, bases, thickeners, excipients, lubricants, binding agents, disintegrating agents, coating agents, corrigents and the like.

Specific examples include water, lactose, sucrose, fructose, glucose, mannitol, sorbitol and other sugars and sugar alcohols, crystalline cellulose, methylcellulose, ethylcellulose, hydroxypropylcellulose, low substituted hydroxypropylcellulose, hydroxypropylmethylcellulose, hydroxypropylmethylcellulose phthalate, hydroxypropylmethylcellulose acetate succinate, carmellose, carmellose calcium, carmellose sodium, croscarmellose sodium, carboxymethylethylcellulose, cellulose acetate phthalate and other celluloses and related derivatives, corn starch, wheat starch, rice starch, potato starch, dextrin, pregelatinized starch, partly pregelatinized starch, hydroxypropyl starch, sodium carboxymethyl starch, cyclodextrin, pullulan and other starches and related derivatives, agar, sodium alginate, acacia, gelatin, collagen, shellac, tragacanth, xanthan gum and other natural polymers (seaweeds, plant mucilage, proteins and the like), polyvinylpyrrolidone, aminoalkyl methacrylate copolymer, methacrylic acid copolymer, carboxyvinyl polymer, polyvinyl alcohol, dimethylpolysiloxane and other synthetic polymers, olive oil, cacao butter, carnauba wax, beef tallow, hydrogenated oil, soybean oil, sesame oil, camellia oil, paraffin, liquid paraffin, yellow beeswax, white petrolatum, coconut oil, microcrystalline wax and other oils and fats, stearic acid, aluminum stearate, calcium stearate, magnesium stearate, triethyl citrate, triacetine, medium chain fatty acid triglyceride, hard fat, isopropyl myristate and other fatty acids and derivatives thereof, glycerin, stearyl alcohol, cetanol, propylene glycol, macrogol and other alcohols and polyvalent alcohols, zinc oxide, dibasic calcium phosphate, precipitated calcium carbonate, synthetic aluminum silicate, silicon dioxide anhydride, kaolin, dried aluminum hydroxide gel, synthetic hydrotalcite, titanium oxide, talc, bentonite, magnesium aluminometasilicate, aluminum potassium sulfate, bismuth subgallate, bismuth subsalicylate, calcium lactate, sodium bicarbonate and other inorganic substances and metal salt compounds, sucrose esters of fatty acid, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol and other surfactants, dyes, perfumes and the like.

Examples of intervention therapy bases include stents, artificial blood vessels and the like.

The administered dose of the preparation for inhibiting local invasion of malignant tumors and for encapsulating malignant tumor tissues of the present invention varies depending on the patient's weight, disease's property and condition, but is for example 1 through 20 batroxobin units (abbreviated as BU) of batroxobin once per day in the case of an adult.

The batroxobin unit described herein is a unit representing an enzyme activity of batroxobin and such an activity that the coagulation of plasma is taken place in 19.0±0.2 seconds when 0.1 ml of a batroxobin solution is added to 0.3 ml of standard human plasma containing citric acid at a temperature of 37° C. is defined as 2 BU.

The preparation for inhibiting local invasion of malignant tumors and for encapsulating malignant tumor tissues of the present invention is preferably administered by diluting the batroxobin appropriately and administering it by intravenous drip or by intravenous, arterial, intramuscular or local administration.

The acute toxicity ($LD_{50}$ (BU/kg)) of batroxobin in mice, rats, rabbits and dogs is shown in Table 1 below. Acute toxicity studies were conducted by intravenous administration of batroxobin, in accordance with the methods described in the literature (Pharmacometrics 25:339-346, 1983).

TABLE 1

Acute toxicity of batroxobin (i.v.)

| Animal Species | $LD_{50}$ Value(BU/kg) |
|---|---|
| Mouse (ddy) | 192-210 |
| Rat (Wistar) | 105-110 |
| Rabbit (NW) | >300 |
| Dog (mongrel) | 190-208 |

The present invention is explained in detail below using examples, but the present invention is not limited by these examples.

EXAMPLE 1

Inhibitive Effect of Batroxobin on Local Invasion of Melanoma

B16-BL6 malignant melanoma cells (solid cancer cells, Academy of Chinese Medical Sciences, Beijing, China) derived from mice with a property of high degree of local invasion, which were subcultured in C57BL/6j mice (Animal Institute of Academy of Medical Sciences, Beijing, China), and were suspended in physiological saline to prepare a melanoma cell suspension with a concentration of $5\times10^6$/ml. 0.2 ml of the resulting melanoma cell suspension was inoculated subcutaneously into the right dorsum of 7-week-old (weight 18 through 20 g) male C57BL/6j mice to prepare tumor-bearing mice.

The established tumor-bearing mice were assigned randomly to a control group (5 mice) and a batroxobin group (10 mice), and which were treated. The mice in the batroxobin group were given intraperitoneal injections of 40 BU/kg of batroxobin once every other day from the $4^{th}$ through the $20^{th}$ day after tumor cell inoculation. The mice in the control group were given intraperitoneal administrations of the same volume of physiological saline (2 ml/kg) instead of batroxobin. At the terminal of the experiment (20 days after tumor inoculation), tissue samples were taken including tumor tissue of solid tumors and the surrounding skin and muscle, and fixed with formalin, then fixed samples were embedded in paraffin, and prepared as hematoxylin-eosin stained samples. The resulting samples were observed under an optical microscope, and the inhibitive effect of batroxobin on the local invasion of the malignant tumors was evaluated.

(1) Microscopic Observation

Figure 2:
FIG. 2 is a microscopic photo of solid cancer tissues of a B16-BL6 melanoma tumor-bearing mouse in batroxobin group.
Figure 2:

FIG. 1 shows a microscopic photo (magnification, 200×) from the control group. FIG. 2 shows a microscopic photo (magnification, 100×) from the batroxobin group (top: encapsulation around tumor tissues, bottom: encapsulation around tumor tissues (from different mouse)).

In the control group, the melanoma cells (T) and surrounding skin or muscle (M) were closely connected, so that it would be difficult to separate the melanoma tissue from the muscle (FIG. 1). This indicated that capsule-like tissue had not been formed.

On the other hand, in the batroxobin group, capsule-like tissue (connective tissue) appeared between the melanoma cells (T) and muscle (M). Invasion of the melanoma cells (T) was restricted due to the presence of this capsule-like tissue, and there was almost no local invasion into subcutaneous connective tissue or flank muscle (FIG. 2, top and bottom) Moreover, in the batroxobin group, the presence of capsule-like tissue means that the melanoma tissue was not closely connected to the surrounding skin and muscle. So this means that the tumor tissues could be easily separated from the skin and muscle and extirpated as a whole.

(2) Quantitative Evaluation of Local Invasion

Local invasion of melanoma cells was evaluated according to the presence or absence of local invasion into the flank muscle layer (positive: local invasion present). The presence or absence of capsule-like tissue surrounding the melanoma tissue (positive: capsule-like tissue present) was also evaluated. The results are shown in Table 2.

TABLE 2

Inhibitive effect of batroxobin on local invasion of subcutaneously transplanted B16-BL6 melanoma

| Treatment group | Local invasion in flank muscle layer (positive/total (%)) | Capsule-like tissue (positive/total (%)) |
|---|---|---|
| Control | 3/5 (60%) | 1/5 (20%) |
| Batroxobin | 0/10 (0%)* | 9/10 (90%)* |

*$P < 0.05$ compared with control group

As shown in Table 2, there is a significant difference between the control and the batroxobin group in the inhibition of local invasion and formation of capsule-like tissue. These results show that batroxobin can effectively inhibit local invasion of melanoma, and can cause or promote formation of capsule-like tissue around melanoma tissues.

EXAMPLE 2

Inhibitive Effect of Batroxobin on Local Invasion of Lung Cancer

LA795 pulmonary adenoma cells (solid cancer cells, Academy of Chinese Medical Sciences, Beijing, China) derived from mice with a property of high degree of local invasion, which were subcultured in male T739 mice (Animal Institute of Academy of Medical Sciences, Beijing, China), and were suspended in physiological saline to prepare a lung cancer cell suspension with a concentration of $5\times10^6$/ml. 0.2 ml of the resulting lung cancer cell suspension was inoculated subcutaneously into the right dorsum of 7-week-old (weight 18 through 20 g) male T739 mice to prepare lung cancer tumor-bearing mice.

The established lung cancer tumor-bearing mice were assigned randomly to a control group (18 mice) and a batroxobin group (18 mice), and which were treated. The mice in the batroxobin group were given intramuscular injections of 40 BU/kg of batroxobin once every other day from the $2^{nd}$ through the $18^{th}$ day after tumor cell inoculation. The mice in the control group were given intramuscular injections of the same volume of physiological saline (2 ml/kg) instead of batroxobin. At the terminal of the experiment (19 days after tumor inoculation), tissue samples were taken including tumor tissue of solid cancers and the surrounding skin and muscle, and fixed with formalin, then fixed samples were embedded in paraffin, and prepared as hematoxylin-eosin stained samples. The resulting samples were observed under an optical microscope, and the inhibitive effect of batroxobin on the local invasion of the malignant tumors was evaluated.

(1) Microscopic Observation

Figure 3:
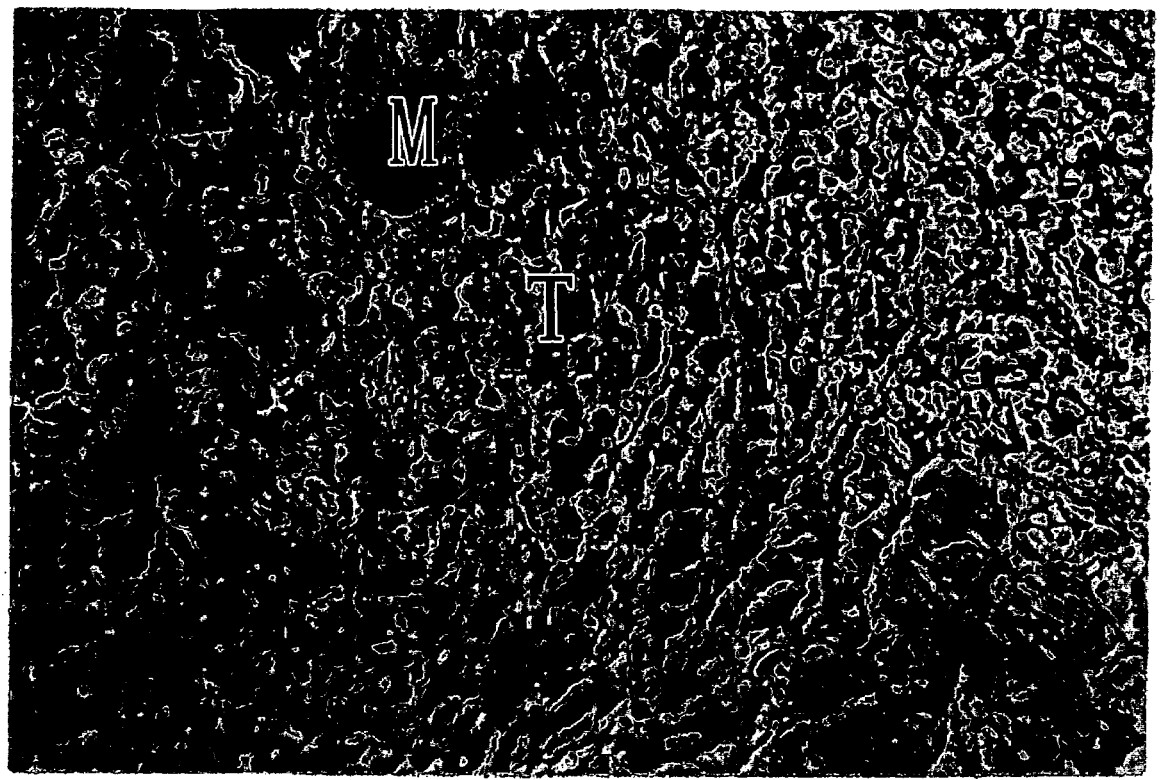
FIG. 3 is a microscopic photo of solid cancer tissues of an LA795 lung cancer tumor-bearing mouse in control group.
Figure 4:
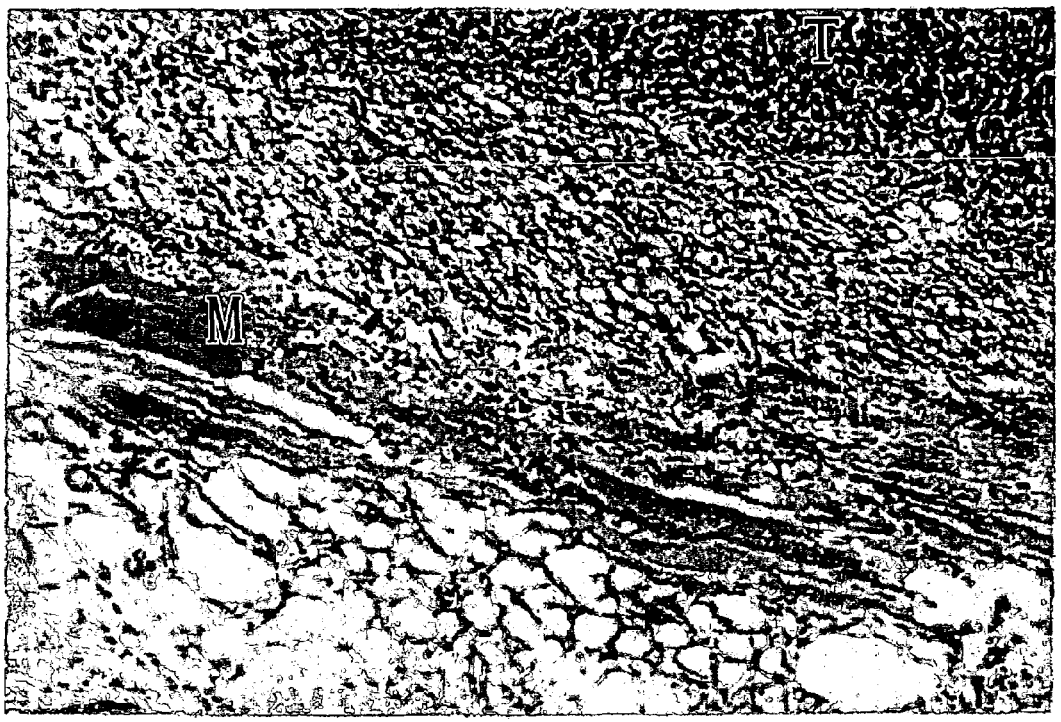
FIG. 4 is a microscopic photo of solid cancer tissue of an LA795 lung cancer tumor-bearing mouse in batroxobin group.
Figure 4:
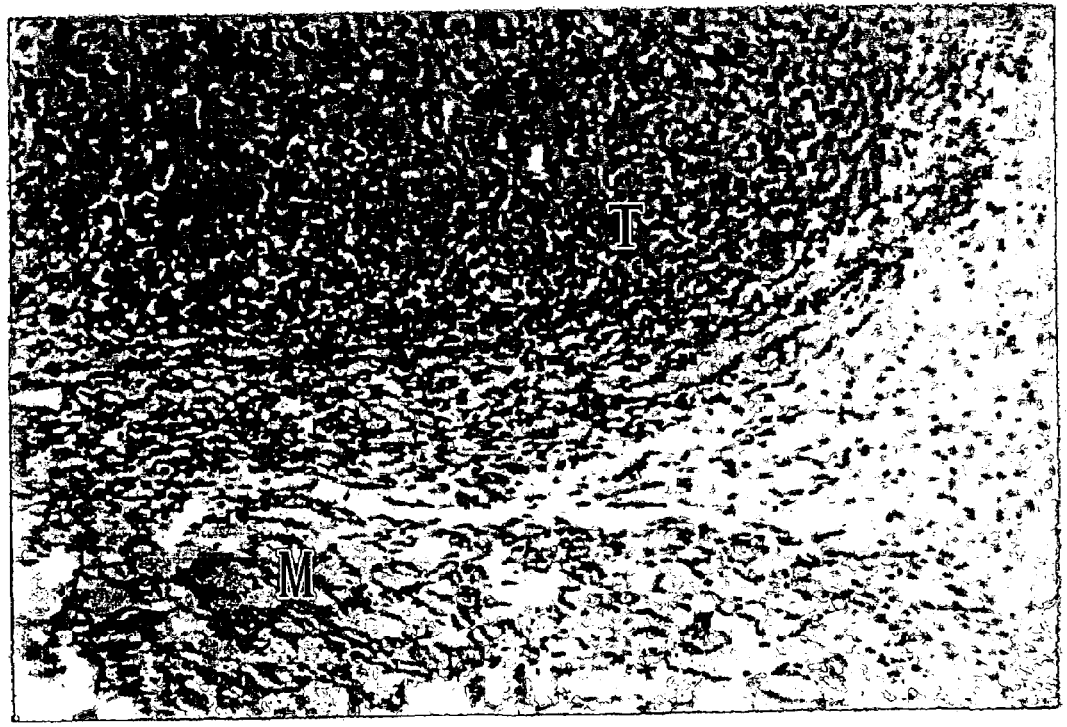

FIG. 3 shows a microscopic photo (magnification, 200×) from the control group. FIG. 4 shows a microscopic photo (magnification, 100×) from the batroxobin group (top: encapsulation around tumor tissues, bottom: encapsulation around tumor tissues (from different mouse)).

In the control group, the lung cancer cells (T) and surrounding muscle (M) were closely mixed together so that it would be almost impossible to separate the solid lung cancer tissue from the muscle (FIG. 3). This indicated that capsule-like tissue had not been formed.

On the other hand, in the batroxobin group, capsule-like tissue (connective tissue) appeared between the lung cancer cells (T) and muscle (M). Invasion of the lung cancer cells (T) is restricted due to the presence of this capsule-like tissue, and there was almost no local invasion into the subcutaneous connective tissue or flank muscle. Specifically, solid lung cancer cells (T) appear in the upper right of the top photo in FIG. 4, while muscle tissues (M) appears on a slant in the middle of the figure with capsule-like tissue in between the two. The top half of the bottom photo in FIG. 4 is occupied by solid lung cancer cells (T), while the bottom half is muscle tissues (M). Capsule-like tissue appears between this cancer tissues and muscle tissues. Moreover, in the batroxobin group, the presence of capsule-like tissue means that the cancer tissues are not closely connected to the surrounding skin and muscle, so that the cancer tissues could be easily separated from the skin and muscle and extirpated as a whole.

(2) Quantitative Evaluation of Local Invasion

Local invasion of lung cancer cells was evaluated according to the presence or absence of local invasion into the flank muscle layer (positive: local invasion present). The presence or absence of capsule-like tissue around the lung cancer tissues (positive: capsule-like tissue present) was also evaluated. The results are shown in Table 3.

TABLE 3

Inhibitive effect of batroxobin on local invasion in subcutaneously transplanted LA795 lung cancer

| Treatment group | Local invasion in flank muscle layer (positive/total (%)) | Capsule-like tissue (positive/total (%)) |
|---|---|---|
| Control | 14/18 (77.8%) | 4/18 (22.2%) |
| Batroxobin | 6/18 (33.3%)* | 10/18 (55.6%)* |

*P < 0.05 compared with control group

As shown in Table 3, there is a significant difference between the control group and the batroxobin group in the inhibition of local invasion and formation of capsule-like tissue. These results show that batroxobin can effectively inhibit local invasion of lung cancer, and can cause or promote the formation of capsule-like tissue around lung cancer tissues.

INDUSTRIAL APPLICABILITY

As shown in the Examples, the present invention can effectively inhibit local invasion of malignant tumors and cause or promote the formation of capsule-like tissue around malignant tumor tissues. Because local invasion is inhibited, less tissue needs to be extirpated during surgical treatment of malignant tumors, and making surgery easier. Moreover, the capsule-like tissue that forms around malignant tumor tissues facilitates the complete extirpation of malignant tumor tissues; The invention can be advantageously used to prevent tumor recurrence due to residual invading malignant tumor cells, which have been a cause of incomplete tumor extirpation in the prior-art of past. Radiation exposure can also be reduced when using radiation therapy because less area of tumor tissues needs to be exposed to radiation.

Consequently, the present invention can be used as a preparation for inhibiting local invasion of malignant tumors and for encapsulating malignant tumor tissues.

The invention claimed is:

1. A method of causing or promoting the formation of encapsulating tissue around tumor tissues to form a barrier between malignant tumor tissues and normal tissues in a patient by administering an effective amount of batroxobin to the patient, through a procedure selected from the group consisting of intravenous drip, intravenous, arterial, intramuscular, or local administration.

2. The method according to claim 1, wherein the malignant tumors are epithelial malignant tumors.

3. The method according to claim 1, wherein the malignant tumors are non-epithelial malignant tumors.

4. The method according to claim 1, wherein the malignant tumors are malignant tumors derived from neural tissue.

5. The method according to claim 1, wherein the malignant tumor is melanoma or lung cancer.

6. A method of encapsulating malignant tumor tissues in a patient by administering an effective amount of batroxobin to the patient through a procedure selected from the group consisting of intravenous drip, intravenous, arterial, intramuscular or local administration, thereby and causing or promoting the formation of encapsulating tissues as a barrier between malignant tumor tissues and normal tissues.

7. The method according to claim 6, wherein the malignant tumors are epithelial malignant tumors.

8. The method according to claim 6, wherein the malignant tumors are non-epithelial malignant tumors.

9. The method according to claim 6, wherein the malignant tumors are malignant tumors derived from neural tissue.

10. The method according to claim 6, wherein the malignant tumor is melanoma or lung cancer.

* * * * *